US008523848B2

(12) United States Patent
Fried et al.

(10) Patent No.: US 8,523,848 B2
(45) Date of Patent: Sep. 3, 2013

(54) NON-INVASIVE LASER VASECTOMY

(75) Inventors: Nathaniel M. Fried, Concord, NC (US); Christopher M. Cilip, Charlotte, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 125 days.

(21) Appl. No.: 13/123,051

(22) PCT Filed: Oct. 8, 2009

(86) PCT No.: PCT/US2009/059967
§ 371 (c)(1),
(2), (4) Date: Aug. 25, 2011

(87) PCT Pub. No.: WO2010/042698
PCT Pub. Date: Apr. 15, 2010

(65) Prior Publication Data
US 2011/0301583 A1    Dec. 8, 2011

Related U.S. Application Data

(60) Provisional application No. 61/103,671, filed on Oct. 8, 2008.

(51) Int. Cl.
*A61B 18/20* (2006.01)
(52) U.S. Cl.
USPC ................................. 606/9; 606/10
(58) Field of Classification Search
USPC ....................... 606/9, 10; 128/898
See application file for complete search history.

(56) References Cited

U.S. PATENT DOCUMENTS

| 4,920,982 A * | 5/1990 | Goldstein .................... 128/842 |
| 5,611,794 A | 3/1997 | Sauer et al. |
| 5,865,835 A | 2/1999 | Lolagne |
| 5,897,551 A | 4/1999 | Everett et al. |

(Continued)

FOREIGN PATENT DOCUMENTS

| EP | 0 480 293 A1 | 4/1992 |
| FR | 2 392 774 A1 | 12/1978 |

(Continued)

OTHER PUBLICATIONS

A. Chandra, "Surgical sterilization in the United States: prevalence and statistics, 1965-1995," Vital Heath Stat., vol. 23(20), pp. 1-41, 1998.

(Continued)

*Primary Examiner* — Bill Thomson
*Assistant Examiner* — Jeffrey Lipitz
(74) *Attorney, Agent, or Firm* — Summa, Additon & Ashe, P.A.

(57) ABSTRACT

The present invention presents novel methods for performing noninvasive vasectomies in animals, including humans, and vasectomy clamps for use in such procedures. The invention further presents an apparatus for use in noninvasive male sterilization procedures. More specifically, the invention presents the application of lasers for noninvasive thermal coagulation and occlusion of the vas. Non-contact cooling of the tissue surface, for example, via cryogen or other cooling spray, prevents scrotal skin burns during the procedure. Both the laser radiation and cooling spray are delivered in a non-contact mode to the tissue. This procedure also preserves the surgical field-of-view, potentially allowing the urologist to visually monitor the skin surface during subsurface heating of the vas and preventing the formation of scrotal skin burns.

20 Claims, 7 Drawing Sheets

(56) References Cited

U.S. PATENT DOCUMENTS

| | | | |
|---|---|---|---|
| 6,039,729 | A | 3/2000 | Durville et al. |
| 6,599,256 | B1 | 7/2003 | Acker et al. |
| 6,852,082 | B2 | 2/2005 | Strickberger et al. |
| 2007/0260269 | A1 | 11/2007 | Marmar |
| 2008/0105265 | A1 | 5/2008 | Pannell et al. |
| 2011/0301583 | A1 | 12/2011 | Fried et al. |

FOREIGN PATENT DOCUMENTS

| | | |
|---|---|---|
| WO | 01/19260 A1 | 3/2001 |
| WO | 2008/058056 A2 | 5/2008 |
| WO | 201004268 A2 | 4/2010 |

OTHER PUBLICATIONS

W. B. Miller, R. N. Shain, and D. J. Pasta, "Tubal sterilization or vasectomy: how do married couples make the choice," Fertil. Steril., vol. 56, pp. 278-284, 1991.

N. W. Hendrix, S. P. Chauhan, and J. C. Morrison, "Sterilization and its consequences," Obstet. Gynecol. Surv., vol. 54, pp. 766-777, 1999.

R. N. Shain, W. B. Miller, and A. E. Holded, "Factors associated with married women's selection of tubal sterilization and vasectomy," Fertil. Steril., vol. 43, pp. 234-244, 1985.

M. Goldstein, "Surgical management of male infertility and other scrotal disorders," In Campbell's Urology, P. C. Walsh, A. B. Retik, E. D. Vaughan, and A. J. Wein AJ, eds. Philadelphia: W. B. Saunders, vol. 2, pp. 1533-1587, 1998.

W. H. Weiske, "Vasectomy," Andrologia, vol. 33(3), pp. 125-134, 2001.

G. L. Smith, G. P. Taylor, and K. F. Smith, "Comparative risks and costs of male and female sterilization," Am. J. Public Health, vol. 75(4), pp. 370-374, 1985.

L. T. Strauss, C. M. Huezo, D. G. Kramer, R. W. Rochat, P. Senanayake, and G. L. Rubin, "Sterilization-associated deaths: a global survey," Int. J. Gynaecol. Obstet., vol. 22, pp. 67-75, 1984.

G. C. Denniston, "Vasectomy by electocautery: outcomes in a series of 2,500 patients," J. Fam. Pract., vol. 21(1), pp. 35-40, 1985.

P. M. Alderman, "Complications in a series of 1224 vasectomies," J. Fam. Pract., vol. 33, pp. 579-584, 1991.

P. J. Schwingl and H. A. Guess, "Safety and effectiveness of vasectomy," Fertil. Steril., vol. 73(5), pp. 923-936, 2000.

S. Li, M. Goldstein, J. Zhu, and D. Huber, "The no-scalpel vasectomy," J. Urol., vol. 145, pp. 341-44, 1991.

R. Ramli, C. Chung, N. M. Fried, N. Franco, M. Hayman, "Nd:YAG Laser Irradiation in Combination with Contact Tissue Cooling for Creation of Subsurface Thermal Lesions," Proc. of SPIE vol. 5686, pp. 183-187 (2005).

N. M. M Fried, W. Roberts, Y. D. Sinelnikov, E. J. Wright, S. B. Solomon, "Focused Ultrasound Ablation of the with Epididymis with Use of Thermal Measurements in a Canine Model," Fertility and Sterility, vol. 78, No. 3, Sep. 2002.

W. W. Roberts, E. J. Wright, N. M. Fried, T. Nicol, T. W. Jarrett, L. R. Kavoussi, S. B. Solomon, "High-Intensity Focused Ultrasound Ablation of the Epididymis in a Canine Model: A Potential Alternative to Vasectomy," J. of Endourology, vol. 16, No. 8, Oct. 2002.

J. O. Esho, G. W. G W Ireland, and A. Cass, "Comparison of ligation and fulguration methods," Urology, vol. 3(3), pp. 337-338, 1974.

S. S. Schmidt and T. M.Minckler, "The vas after vasectomy: comparison of cauterization methods," Urology, vol. 40(5), pp. 468-470, 1992.

T. R. L. Black, D. S. Gates, K. Lavely, and P. Lamptey, "The percutaneous electrocoagulation vasectomy technique—a comparative trial with the standard incision technique at marie stopes house, London," Contraception, vol. 39, pp. 359-368, 1989.

N. M. Fried, Y. D. Sinelnikov, B. Pant, W. W. Roberts, and S. B. Solomon, "Noninvasive vasectomy using a focused ultrasound clip: Thermal measurements and simulations," IEEE Trans. Biomed. Eng., vol. 48(12), pp. 1453-1459, 2001.

W. W. Roberts, D. Y. Chan, N. M. Fried, E. J. Wright, T. Nichol, T. W. Jarrett, L. R. Kavoussi, and S. B. Solomon, "High intensity focused ultrasound ablation of the vas deferens in a canine model," J. Urol., vol. 167, pp. 2613-2617, 2002.

A. Shafik, "Electrovasogram: a canine study of the electromechanical activity of the vas deferens," Urology, vol. 46(5), pp. 692-696, 1995.

Notification of Transmittal of the International Search Report and Written Opinion of counterpart Application No. PCT/US2009/059967 mailed Jun. 8, 2010, 18 pages.

C. M. Cilip, J. P. Jarrow, N. M. Fried, "Noninvasive Laser Vasectomy: Preliminary Ex Vivo Tissue Studies," Lasers in Surgery and Medicine 41:203-207 (2009).

C. M. Cilip, J. P. Jarow, N. M. Fried, "Noninvasive Laser Coagulation of the Canine Vas Deferens, Ex Vivo," Proc. of SPIE vol. 7161 71611O-1 (2009).

R. Ramli, D. Durand, N. M. Fried, "Subsurface Tissue Lesions Created Using an Nd:YAG Laser and Cryogen Cooling," J. of Endourology, vol. 17, No. 10, Dec. 2003.

R. Ramli, D. Durand, N. M. Fried, "Deep Subsurface Thermal Lesions in Tissue using an Nd:YAG Laser and Croygen Spray Cooling: Preliminary In Vitro Results," Proc. of SPIE vol. 5312, pp. 112-116.

R. Ramli, C. Chung, N. M. Fried, N. Franco, M. H. Hayman, "Subsurface Tissue Lesions Created Using an Nd: YAG Laser and a Sapphire Contact Cooling Probe," Lasers in Surgery and Medicine 35:392-396 (2004).

C. Chung, S. Permpongkosol, I. M. Varkarkis, G. Lima, N. Franco, M. H. Hayman, T. Nichol, N. M. Fried, "Laser Probes for Noninvasive Coagulation of Subsurface Tissues," Proc. of SPIE vol. 6078 607822-1 (2006).

U.S. Appl. No. 61/103,671 "Noninvasive Vasectomy," filed Oct. 8, 2008.

Invitation to Pay Additional Fees and Where Applicable, Protest Fee; Annex to Form PCT/ISA/206 Communication Relating to the Results of the Partial International Search of counterpart Application No. PCT/US2009/059967 mailed Mar. 26, 2010, 7 pages [all references cited].

International Preliminary Report on Patentability of counterpart Application No. PCT/US2009/059967 dated Apr. 12, 2011, pp. 1-6.

Gunderrnan et al., The Limited Monopoly "Under the Knife"—Patenting Surgical Procedures; The Rochester Engineer, Feb. 2009; p. 10.

* cited by examiner

NON-INVASIVE LASER VASECTOMY

CROSS-REFERENCE TO RELATED APPLICATIONS

This application claims priority to and incorporates by reference herein U.S. Provisional Patent Application Ser. No. 61/103,671 filed on Oct. 8, 2008 and entitled "Noninvasive Laser Vasectomy." The Application further claims priority to and incorporates by reference herein International Patent Application Number PCT/US2009/059967 filed on Oct. 8, 2009.

STATEMENT REGARDING FEDERALLY SPONSORED RESEARCH

The invention claimed herein was made under U.S. Agency for International Development Contract No. CCP-A-OO-95-00022-02; Grant No. GPO-A-00-05-00022-00, and the United States government has certain rights in the invention.

FIELD OF THE INVENTION

The invention relates to a method of performing noninvasive laser vasectomies and apparatuses used the procedure.

BACKGROUND

Surgical sterilization is currently the most common method of contraception among married couples in the United States [1]. Male sterilization (vasectomy) has a higher success rate, lower morbidity and mortality rate, is less expensive, and easier to perform than female sterilization (tubal ligation) [1-3]. Despite these advantages, however, female sterilization is more commonly performed. Fear of complications related to surgery was frequently cited as the primary reason for a couple choosing tubal ligation instead of vasectomy [1,2,4]. In the U.S., for example, there are approximately 500,000 vasectomies and 1 million tubal ligations performed each year [5]. Worldwide, approximately 40 million men have had a vasectomy [6]. While there have been no reported cases of vasectomy-related deaths in the U.S. [7, 8], there are 10-20 deaths each year due to tubal ligation. Worldwide, these numbers are even greater [8]. Complication rates of vasectomy range from 1-6% and include sterilization failure, hematoma, infection, sperm granuloma, and epididymitis [9-11]. However, several studies have reported much higher rates of infection (12-38%) which may be due primarily to the experience of the physician performing the procedure [5].

During conventional surgical vasectomy, the vas deferens is separated from the spermatic cord vessels and manipulated to a superficial position under the scrotal skin. A needle is used to inject local anesthesia around the vas, producing a vasal nerve block. Then 1-cm-long incisions are made through the vas sheath until the vas is exposed. The vas is delivered and the deferential artery, veins, and nerves are dissected free of the vas and spared. A 1-cm-long vas segment is then removed and the ends of the vas are occluded using thermal cautery, followed by the placement of hemoclips [5].

Although conventional vasectomy is a simple, inexpensive procedure with minimal morbidity, there are several reasons for exploring a noninvasive approach to male sterilization. An incision-less and puncture-less method of male sterilization would eliminate surgery and the associated risks of infection, bleeding, and scrotal pain. This may lead to greater acceptance of vasectomy by men, reducing the morbidity, mortality, and cost associated with tubal ligation. Therefore, there is a clear need for safer, less invasive method to perform vasectomies.

In recent years, the "no-scalpel" vasectomy technique has been developed to minimize complications associated with incision during the procedure [12]. This method eliminates the use of the scalpel, results in fewer hematomas and infections, and leaves a smaller wound than conventional methods [5]. The success of this method is proven by a complete reversal in the ratio of male to female sterilizations, now 3 to 1, in the Szechuan province of China [4]. However, despite the name "no-scalpel-vasectomy", this procedure still requires a puncture through the skin and does not completely eliminate the possibility of bleeding, infection, and scrotal pain. A "no-scalpel" vasectomy technique has also been disclosed in U.S. Pat. No. 4,920,982 to Goldstein; however, this procedure requires a step of inserting a sharp-tipped needle into the scrotum and through a wall of the vas deferens. This procedure too requires a puncture through the skin, thereby exposing the vas deferens, and it does not completely eliminate the possibility of bleeding, infection, and scrotal pain.

A percutaneous approach to vasectomy has also been performed in over 500,000 men using chemical ablation with cyanoacrylate and phenol [13-15]. A needle is placed into the lumen of the vas using a series of tests involving dye injections for confirmation. Although pharmacologic tests of the cyanoacylate-phenol mixture have demonstrated no toxicity, these chemicals are not approved for use in the U.S. Another concern with this method is the great skill involved with gaining percutaneous access to the 300-μm-diameter lumen of the vas deferens.

Thermal methods of vas occlusion have also been studied for producing more reliable permanent vas occlusion. Some of these studies have suggested that thermal destruction of the vas luminal integrity provides more successful prevention of recanalization of the vas than does suture ligation during wound healing, with failure rates decreasing from 1-6% to 0.24% [9,16]. As a result, it is now common for physicians to cauterize the cut ends of the vas as an alternative to ligation. There is also evidence that more uniform thermal necrosis of the vas lumen with hot wire rather than superficial lumen destruction using electrocautery provides more successful results [17]. These studies used thermal techniques in either a minimally invasive surgical or percutaneous approach to vasectomy [9, 17, 18].

The use of ultrasound as a noninvasive technique for vas occlusion has been studied. Ultrasound, however, has many disadvantages, including but not limited to the requirement of a coupling medium, which may obstruct the urologist's field-of-view. Further, focused ultrasound typically creates acorn-shaped lesions with a higher depth-to-with ratio, which is more likely to damage tissue structures immediately surrounding the vas.

BRIEF SUMMARY OF THE INVENTION

The present invention presents novel methods for performing noninvasive vasectomies in animals, including humans, and vasectomy clamps for use in such procedures. The invention further presents an apparatus for use in noninvasive male sterilization procedures.

According to one embodiment of the invention, a method of noninvasive male sterilization is provided, the method comprising steps of positioning the vas deferens in a superficial position under the scrotal skin; cooling at least a portion of the scrotal skin in a target area; and irradiating a region within the target area with a laser. By this method, the vas deferens in that region is thermally coagulated without exposing the vas deferens through the skin (such as, for example, by incision or puncture), thereby minimizing or eliminating completely risks of infection, bleeding, and scrotal pain.

According to another embodiment of the invention, a method of noninvasive male sterilization is provided, the method comprising the steps of grasping the vas deferens and surrounding scrotal skin with an insulated vasectomy clamp to secure a target area within and over a portion of the vasectomy clamp; irradiating a region within the target area with a pulsed laser beam, wherein the vas deferens in that region is thermally coagulated without exposing the vas deferens; and cooling at least a portion of the scrotal skin of the target area with cryogen spray prior to and intermittently during laser pulses.

According to another embodiment of the invention, an apparatus for use in noninvasive male sterilization procedures in which a vas deferens is thermally coagulated with a laser is provided, the apparatus comprising an insulated vasectomy clamp for grasping the vas deferens and surrounding scrotal skin to secure within and over a portion of the vasectomy clamp a target area. The apparatus further comprises a laser for irradiating a region within the target area, wherein the vas deferens in that region is thermally coagulated while remaining enclosed within the scrotal skin, and the apparatus comprises a cooling device for cooling at least a portion of the scrotal skin of the target area.

DETAILED DESCRIPTION

The present invention presents novel methods for performing noninvasive vasectomies in animals, including humans, and vasectomy clamps for use in such procedures. The invention further presents an apparatus for use in noninvasive male sterilization procedures.

Figure 3:
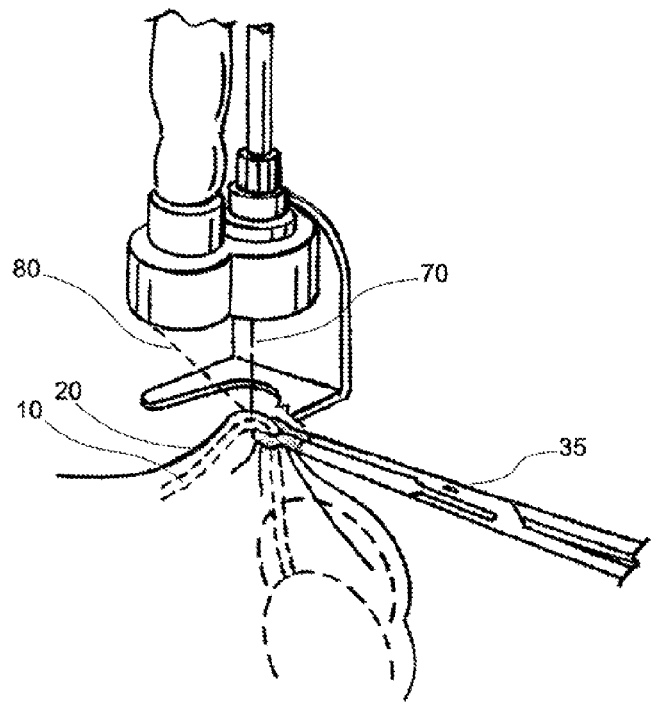
FIG. 3 shows a laser and cooling mechanism for practicing the noninvasive vasectomy of one embodiment of this invention.

In one aspect, the present invention provides noninvasive laser coagulation of the vas as an alternative to ultrasound vas occlusion. A laser-based approach offers several advantages over ultrasound. First, unlike ultrasound, the laser energy can be delivered to the tissue in a non-contact mode without the need for a coupling medium. The methods of the present invention allow a conventional no-scalpel vasectomy approach to be taken for separating and isolating the vas under the skin prior to vasectomy. It also preserves the urologist's field-of-view so he can directly visually monitor the skin surface during subsurface heating of the vas and minimize or prevent the formation of scrotal skin burns. A further aspect of the invention allows the surgeon to create circular lesions that match the geometry of the vas tube, while focused ultrasound typically creates acorn-shaped lesions with a higher depth-to-with ratio, more likely to damage tissue structures immediately surrounding the vas. According to one embodiment of the invention, a method of noninvasive male sterilization is provided, the method comprising steps of positioning the vas deferens in a superficial position under the scrotal skin; cooling at least a portion of the scrotal skin in a target area; and irradiating a region within the target area with a laser. FIG. 3 shows an example of a target area subject to cooling spray 80 in one embodiment of this invention. The target area includes scrotal skin with at least a portion of the vas deferens sufficiently proximate the scrotal skin to be subject to a laser beam 70 without exposing the vas deferens through the skin. The laser beam 70 is directed to a region within the target area such that the energy of the laser beam heats the vas deferens in that region. By this method, the vas deferens in that region is thermally coagulated without exposing the vas deferens through the skin. According to another embodiment of the invention, more than one region on one or both vas deferens is irradiated.

According to another embodiment of the invention, a method of noninvasive male sterilization further includes a step of grasping the vas deferens and surrounding scrotal skin with a vasectomy clamp to secure the target area within and over a portion of the vasectomy clamp prior to irradiating the region of the target area. Securing the scrotal skin and the subject vas deferens over a portion of the vasectomy clamp positions a subject portion of the vas deferens just under the skin. This arrangement provides a clear cross section of the vas deferens for the laser beam 70 to heat. Positioning a cross section of the vas deferens within a laser beam 70 provides a method of thermally coagulating a subject portion of the vas deferens and avoids directing the laser energy down the length of the vas deferens. According to another embodiment, this positioning step comprises rotating the vasectomy clamp to enhance the shallow depth of the vas deferens directly under the skin, making the vas deferens even more readily heated by the laser beam 70. In one embodiment, rotating the clamp positions the scrotal skin and the vas deferens over one of the prongs of the vasectomy clamp to achieve a stable position during the noninvasive laser vasectomy.

Figure 1:
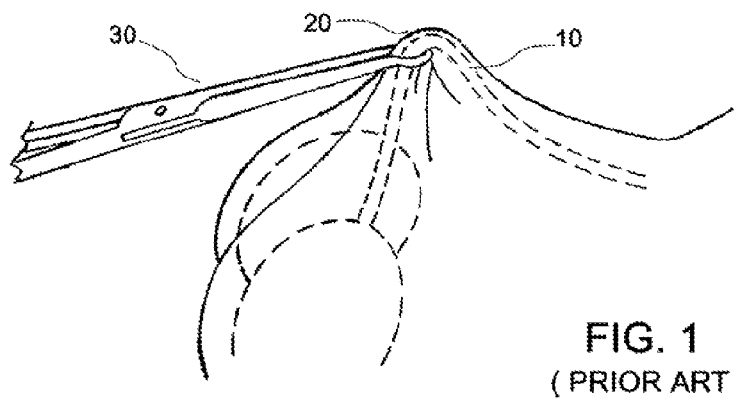
FIG. 1 shows PRIOR ART.
Figure 4:
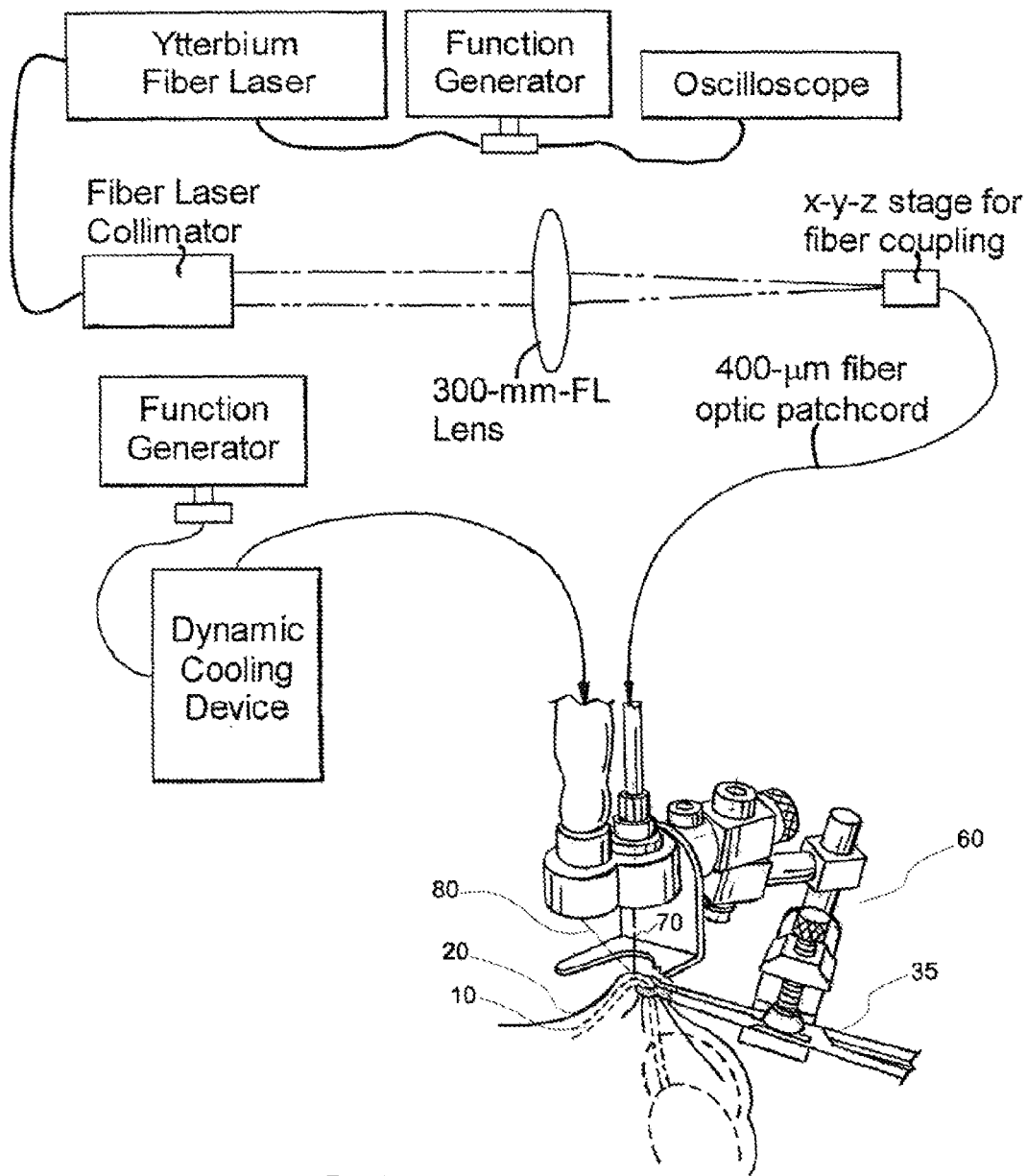
FIG. 4 shows a laser and cooling mechanism and associated equipment for practicing one embodiment of the noninvasive vasectomy disclosed herein.

Manipulation of the vas deferens 10 to a superficial position under the scrotal skin 20 with a standard vasectomy clamp 30 is shown in FIG. 1 (Prior Art). FIGS. 3 and 4 show example setups for two embodiments of the present invention. In these Figures, the vas deferens 10 is separated from the spermatic cord vessels and manipulated to a superficial position under the scrotal skin 20 with an insulated vasectomy clamp 35. As shown in FIGS. 3 and 4, the insulated vasectomy clamp 35 is used to grasp the vas deferens 10 and surrounding scrotal skin 20 to secure a target area within and over a portion of the insulated vasectomy clamp 35 prior to irradiating the region of the target area.

The apparatus of FIG. 4 further comprises a means 60 for holding the vasectomy clamp and positioning the target area under the laser. Without limiting the invention to any one embodiment, FIG. 4 shows the means 60 for holding the vasectomy clamp as a vice that has an adjustable position. As shown in FIG. 4, the user has the option of manually positioning the clamp with the scrotal skin and vas deferens gripped therein before stabilizing the desired clamp position with the means 60. The overall setup of FIG. 4 provides multiple axes of rotation for the means 60 to hold the clamp in the chosen position.

A cooling spray 80 is directed to a portion of the scrotal skin 20 in the target area to cool the skin 20. In the embodiment shown in FIGS. 3 and 4, the target area is an area in which the vas deferens 10 is positioned within and over the vasectomy clamp 35. A region of that target area may be irradiated such that a laser beam 70 extends through a cross-section of the vas deferens 10, rather than longitudinally through the vas deferens 10.

According to one embodiment of the invention, an insulated vasectomy clamp for use in noninvasive male sterilization procedures in which a vas deferens is thermally coagulated with a laser is provided. According to one embodiment, the vasectomy clamp may be thermally insulated along a portion at which the clamp contacts the skin. According to another embodiment, the vasectomy clamp comprises two or more prongs that are thermally insulated.

According to one embodiment, the vasectomy clamp comprises an insulating material that is transparent to near-infrared laser radiation and is also thermally insulating. In another embodiment, the insulating material is thermally insulating and transparent to wavelengths of approximately 700 nm to approximately 1300 nm. According to another embodiment of the invention, the insulating material comprises fluorinated ethylene propylene copolymer, for example, FEP Teflon. The insulating material may be applied to the vasectomy clamp by numerous manufacturing techniques, including but not limited to the use of heat shrinking insulating wraps applied to stainless steel prongs of the clamp.

Figure 2:
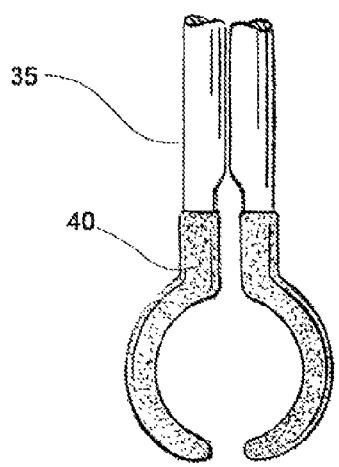
FIG. 2 shows an insulated vasectomy clamp according to one embodiment of the invention.

An insulated vasectomy clamp 35 according to one embodiment of the invention is shown in FIG. 2. The insulated vasectomy clamp 35 includes insulating material 40 on the prongs or, in another embodiment, on along the portion at which the clamp 35 would contact the skin. The vasectomy clamp 35 may comprise prongs substantially forming a ring having an inner diameter of approximately 3 mm to approximately 6 mm; a ring having an inner diameter of approximately 3 mm to approximately 4 mm; a ring having an inner diameter of approximately 3.5 mm to approximately 4 mm; or a ring having an inner diameter of approximately 3.5 mm. One of skill in the art will appreciate that the insulated vasectomy clamp 35 shown in FIG. 2 is one example, but that an insulated vasectomy clamp of any formation that facilitates securing of the vas deferens 10 in a superficial position under the scrotal skin 20 to permit the use of a laser in a region to thermally coagulate the vas deferens 10 in that region without exposing the vas deferens 10 through the skin 20 is encompassed by the invention and may be used.

According to one embodiment of the invention, a portion of the scrotal skin is cooled with a cooling spray 80, for example, a cryogen spray or cold air, or other non-contact cooling means. According to one embodiment of the invention, the cooling spray 80 may be delivered to at least an approximately 2-cm-diameter spot that is substantially concentric with the irradiated region. According to another embodiment, the spray spreads to an area that is approximately 5 to 20 cm in diameter. This spray area includes a portion of the scrotal skin in the target area; however, the spray area is not limited to the skin. Some of the spray may extend beyond the skin to the surrounding environment.

The cooling spray may be applied to cool at least a portion of the scrotal skin in the target area prior to irradiation. According to another embodiment, the laser beam is pulsed and at least a portion of the scrotal skin in the target area is cooled with a spray intermittently during laser pulses. According to a further embodiment, the cooling spray is used to cool the scrotal skin prior to irradiation and intermittently during laser pulses.

The laser emits radiation with a wavelength of approximately 700 nm to approximately 1300 nm. According to one embodiment of the invention, the laser emits radiation with a wavelength of approximately 1075 nm. According to another embodiment, the laser beam is pulsed and the pulse duration is in the range of approximately 0.1 to 1 second. According to other embodiments, the laser has an output power of from about 5 to 15 W, a pulse duration of about 0.1 to 1 second, and a pulse repetition rate of from about 0.1 to 10 Hz can be used.

According to one embodiment of the invention, the irradiated region is approximately 2-4 mm in diameter. According to another embodiment, the irradiated region is approximately 3 mm in diameter.

According to another embodiment of the invention, a method of noninvasive male sterilization is provided, the method comprising the steps of grasping the vas deferens and surrounding scrotal skin with an insulated vasectomy clamp to secure a target area within and over a portion of the vasectomy clamp; irradiating a region within the target area with a pulsed laser beam, wherein the vas deferens in that region is thermally coagulated without exposing the vas deferens; and cooling at least a portion of the scrotal skin of the target area with cryogen spray prior to and intermittently during laser pulses.

According to another embodiment of the invention, an apparatus for use in noninvasive male sterilization procedures in which a vas deferens is thermally coagulated with a laser is provided, the apparatus comprising an insulated vasectomy clamp for grasping the vas deferens and surrounding scrotal skin to secure within and over a portion of the vasectomy clamp a target area. The apparatus further comprises a laser for irradiating a region within the target area, wherein the vas deferens in that region is thermally coagulated while remaining enclosed within the scrotal skin, and the apparatus comprises a cooling device for cooling at least a portion of the scrotal skin of the target area. According to other embodiments, the cooling device directs a cooling spray, cryogen spray, or cold air onto the scrotal skin.

According to another embodiment, the apparatus further comprises a means for holding the vasectomy clamp and positioning the target area under the laser.

In one non-limiting example, Ytterbium fiber laser radiation with a wavelength of 1075 nm, average power of 11.7 W, 1-s pulse duration, 0.5 Hz pulse rate, and 3-mm-diameter spot was synchronized with cryogen cooling of the scrotal skin surface for a treatment time of 60 s.

In another non-limiting example: Scrotal skin and vas tissue was harvested from male dogs immediately after sacrifice for unrelated experiments. The tissue was used in an ex vivo vasectomy model. The tissue was partially submerged in a temperature-controlled saline bath, placed on a hotplate, and maintained at approximately 37° C. A 4.0-mm-ID vasectomy clamp was then used to tightly grasp the vas and surrounding scrotal skin. Table 1 provides a comparison between the normal thickness of the tissue layers and the thicknesses after compression between the vasectomy clamp, as measured using both standard calipers and an optical coherence tomography system (Niris, Imalux, Cleveland, Ohio).

TABLE 1

Canine tissue dimensions (mm).

| | |
|---|---|
| Normal scrotal skin thickness: | 1.8 |
| Compressed scrotal skin thickness: | 1.0 |
| Uncompressed vas wall thickness: | 0.55 |
| Total vas thickness: | 1.3 |
| Vas lumen: | 0.2 |

A 50-W CW Ytterbium fiber laser (Model TLR1075-50, IPG Photonics, Oxford, Mass.) emitted radiation with a wavelength of 1075 nm that was focused with a 300-mm-FL lens into a 400-μm silica fiber optic patchcord. A function generator (Model DS345, Stanford Research Systems, Palo Alto, Calif.) was used to modulate the fiber laser, producing an average fiber output power of 11.7 W, 1-s pulse duration, 0.5 Hz pulse rate, and 3-mm-diameter spot at the scrotal skin surface.

A dynamic cooling device (DCD, Candela Laser Corporation, Wayland, Mass.) was used to deliver the cryogen (halocarbon 134a, 1,1,1,2-tetrafluoroethane, boiling point=−26° C.) to the tissue surface through a solenoid valve. The solenoid valve was externally triggered with a 50-ms-long, inverted 5 V signal from an arbitrary function generator (Model DS345, Stanford Research Systems, Palo Alto, Calif.), and an oscilloscope (Tektronix, Model TDS 1002, Beaverton, Oreg.) was used to view the pulse characteristics. A total of 2 cryogen pulses were used to pre-cool the tissue surface prior to irradiation. During irradiation, the cryogen spray was delivered intermittently between laser pulses with a pulse duration of 60 ms, pulse repetition rate of 0.333 Hz, and a 2-cm-diameter spot size concentric with the laser spot. A summary of the treatment parameters is provided in Table 2, and diagrams of the experimental setup are shown in FIG. 2 (however, the experiments discussed herein were performed on scrotal skin and vas tissue harvested from male dogs immediately after sacrifice for unrelated experiments).

TABLE 2

Summary of Laser and Cooling Parameters

| Laser Parameters | | Cooling Parameters | |
|---|---|---|---|
| Wavelength (nm): | 1075 | Pulse Duration (ms): | 60 |
| Average Power (W): | 11.7 | Pulse Repetition Rate (Hz): | 0.333 |
| Pulse Duration (s): | 1.0 | Spot Diameter (mm) | 20 |
| Pulse Repetition Rate (Hz): | 0.5 | Number of Pre-Cooling Pulses: | 3 |
| Duty Cycle: | 1:1 | Total Number of Pulses: | 23 |
| $1/e^2$ Spot Diameter (mm): | 3.0 | Total Treatment Time (s): | 70 |

Figure 5:
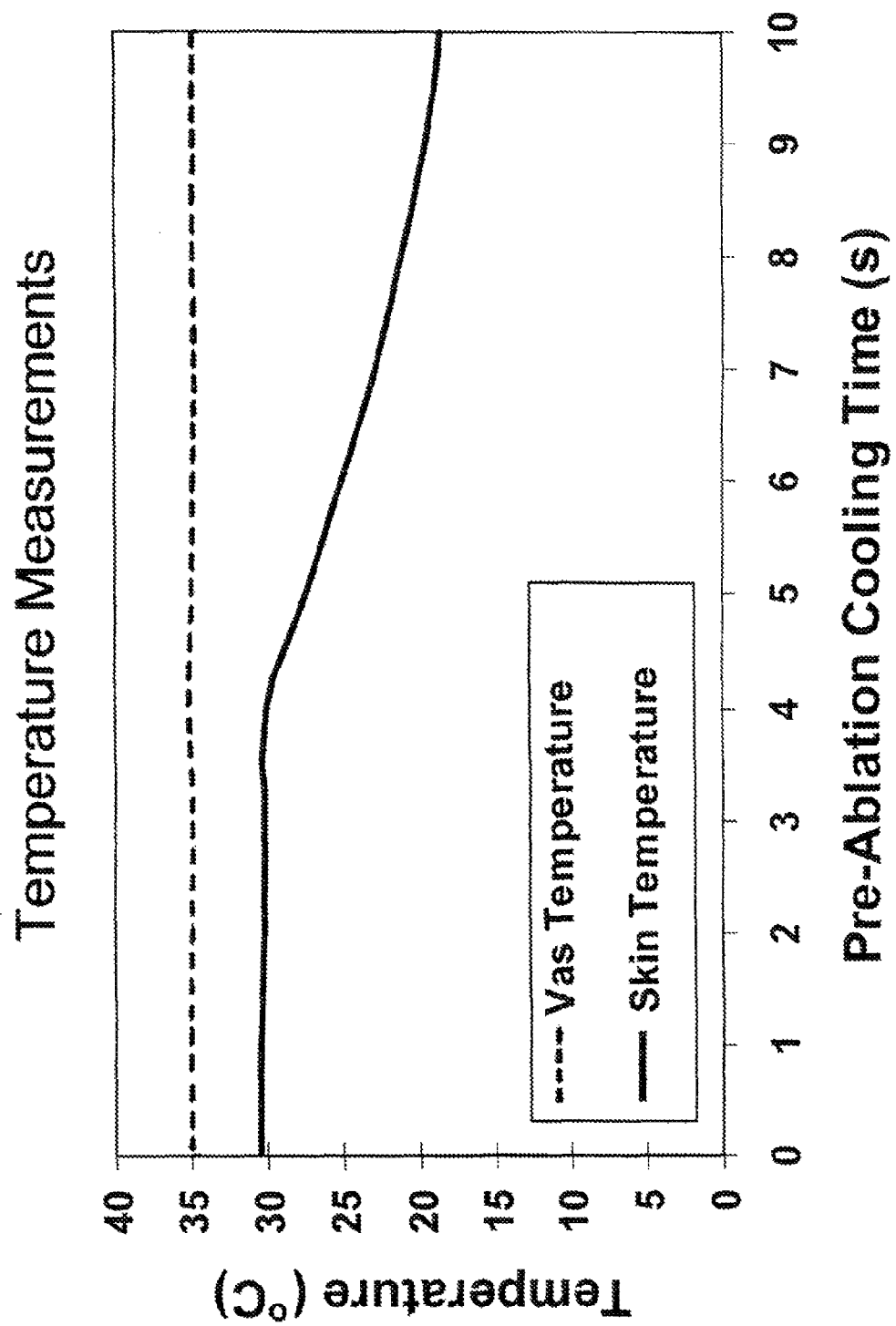
FIG. 5 presents temperature vs. time graph for scrotal skin surface (solid line) and vas (dotted line) during pre-ablation cooling phase. The scrotal skin surface cools down to approximately 20° C., while the vas remains at 35° C. This separation in temperatures provides a therapeutic window in which to heat and coagulate the vas without causing thermal damage to the surface.

Temperature measurements were conducted during the pre-ablation cooling phase using insulated micro-thermocouples (Cu—Cn, 125-μm-diameter, 30-ms response time, Omega Corporation, Stamford, Conn.) interfaced to a personal computer with automated acquisition of temperature vs. time data. The thermocouples were placed at the skin surface and inside the vas lumen at approximately 1.5 mm below the skin surface. Temperature measurements were recorded during the pre-ablation cooling phase at a sampling rate of 1 s, as shown in FIG. 5.

Several indicators were used to confirm thermal occlusion of the vas, including gross and histologic analysis of the vas and burst pressure measurements. Thermal lesions in the vas measured approximately 2 mm diameter by 3 mm length, without any evidence of scrotal skin burns. Burst pressures for the coagulated vas measured about 300 mm Hg, over twice as high as the approximately 140 mm Hg that the vas experiences during ejaculation.

Figure 6:
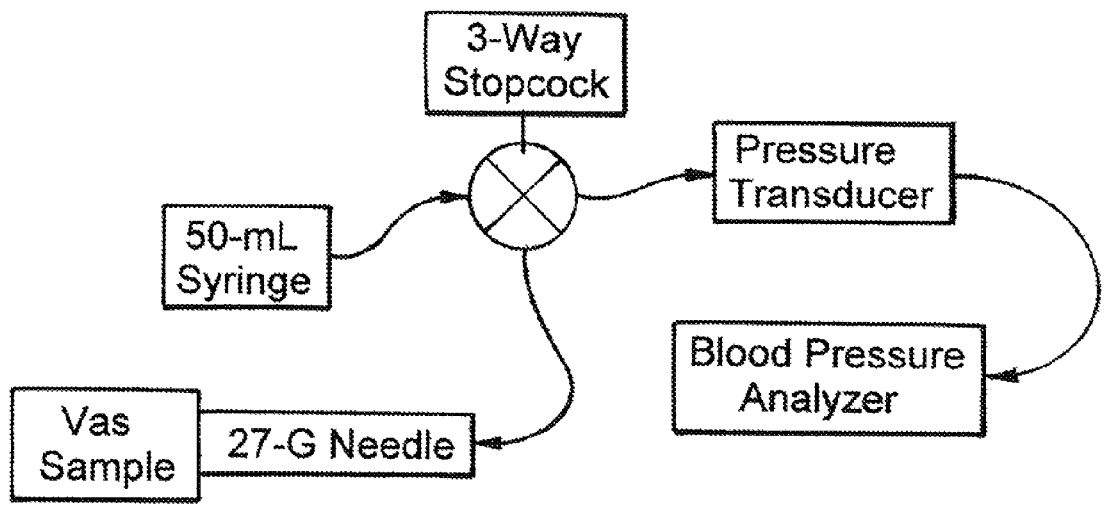
FIG. 6 shows a setup for conducting vas burst pressure measurements.

Vas burst pressure measurements were performed to quantify the degree of closure of the thermally coagulated vas. As shown in FIG. 6, the ports of a 3-way stopcock were connected to a 50 mL syringe, pressure transducer, and hypodermic needle. The syringe was filled with water which was also distributed throughout the entire system. The vas was attached to a 27-G (406-μm-OD) hypodermic needle and clamped with hemostats. A pressure analyzer unit was calibrated to zero setting. Water from the syringe was then slowly pumped into the vas tube, resulting a pressure reading that elevated over a 20 s time period until the vas burst open and the pressure dropped precipitously.

A total of 20 vas were thermally coagulated with 10 vas processed for histologic measurements and 10 vas used for burst pressure measurements. The mean±standard deviation (S.D.) was calculated for each parameter measured.

TABLE 3

Burst Pressure Measurements (mmHg)

| | |
|---|---|
| Resting Pressure: | 5 ± 1 |
| Ejaculation Pressure: | 136 ± 29 |
| Burst Pressure of Coagulated Vas (Ex Vivo): | 295 ± 72 |
| Burst Pressure of Coagulated Vas (In Vivo): | 283 ± 34 |
| Burst Pressure of Scarred Vas (21 Days): | 260 ± 77 |

Figure 7:
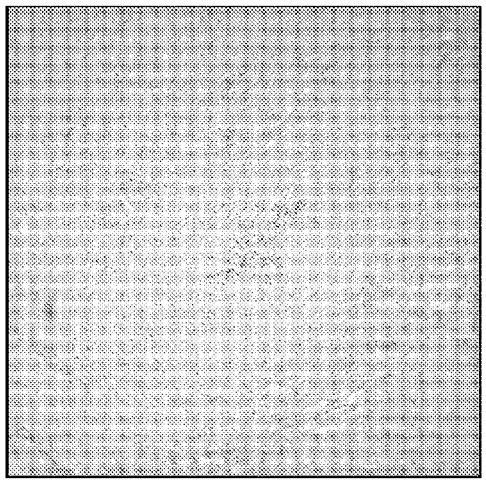
FIG. 7 illustrates H&E-stained histologic cross-section of vas after laser coagulation.
Figure 8:
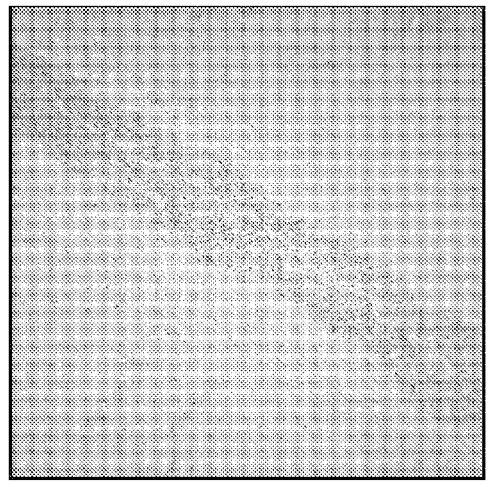
FIG. 8 illustrates H&E-stained histologic longitudinal section of vas after laser coagulation, demonstrating complete vas occlusion.
Figure 9:
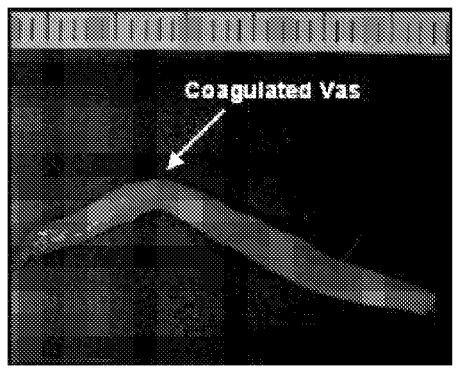
FIG. 9 illustrates gross image of the thermally coagulated region of the vas (ruler bar=1 mm increments).

Thermal coagulation and occlusion of the vas was achieved in all samples with one exception. If the 3-mm-diameter laser beam was not correctly centered within the 4-mm-ID ring of the vasectomy clamp, skin burns were observed from absorption and scattering of the laser radiation off of the steel clamp, and the vas was incompletely coagulated. Gross measurements and histologic analysis were both used to assess the thermal lesion dimensions on the vas. Gross analysis was more accurate due to the difficulty in achieving precise longitudinal histologic sections through the vas lumen. Vas lesion dimensions measured 2.0±0.3 mm diameter by 3.0±0.9 mm length, without any visual evidence of skin damage (Table 4). Analysis of histologic cross-sections and longitudinal sections of the vas demonstrated complete closure of the vas lumen (FIGS. 7 (cross-section) and 8 (longitudinal section)). In these Figures, the darker areas represent the hollow, porous parts of the vas lumen. The lighter areas show the vas wall tissue. The lighter portions of the image, showing the vas deferens tissue, are interspersed throughout the darker regions that would ordinarily represent a hollow spermatic duct absent the laser surgery. FIGS. 7 and 8, therefore, illustrate that the noninvasive laser surgery described herein has effectively coagulated the vas deferens pathway and closed the vas lumen. FIG. 9 presents a gross image of the thermally coagulated region of the vas (ruler bar=1 mm increments). The targeted area of the vas consistently demonstrated significant blanching, hardening, and shrinkage, all characteristic indicators of thermally coagulated tissue.

TABLE 4

Dimensions of Thermal Lesions in the Canine Vas

| Parameter | Lesion |
|---|---|
| Native Vas Width (mm): | 2.8 ± 0.3 |
| Coagulated Vas Width (mm): | 2.0 ± 0.3 |
| Reduction in Vas Width (%): | 30 ± 8 |
| Vas Lesion Length (mm): | 3.0 ± 0.9 |

FIG. 5 shows temperature versus time data for the scrotal skin surface and vas during the pre-ablation cooling phase of the study. The scrotal skin surface cools down to approximately 20° C., while the vas remains at 35° C. This separation in temperatures provides a therapeutic window in which to heat and coagulate the vas without causing thermal damage to the surface.

The resting intravasal pressure (IVP) of the vas is approximately 7±3 cm $H_2O$ (5±1 mm Hg) and the IVP during ejaculation reaches 185±39 cm $H_2O$ (136±29 mm Hg) [21]. The bursting pressure of the coagulated vas samples averaged 401±98 cm $H_2O$ (295±72 mm Hg), significantly above the resting and ejaculation pressures that the vas physiologically experiences.

Vas thermal lesion dimensions measured 2.0±0.3 mm diameter by 3.0±0.9 mm length, without skin damage. The coagulated vas bursting pressure measured 295±72 mm Hg, significantly higher than typical vas ejaculation pressures of 136±29 mm Hg. The present working example shows noninvasive thermal coagulation and occlusion of the vas is feasible through laser techniques.

Figure 10:
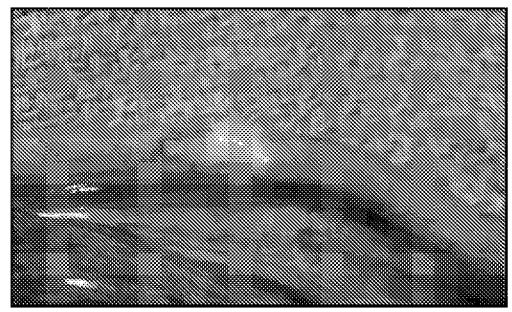
FIG. 10 is a photograph of a thermally coagulated canine vas after being subject to the noninvasive laser vasectomy disclosed herein.
Figure 11:
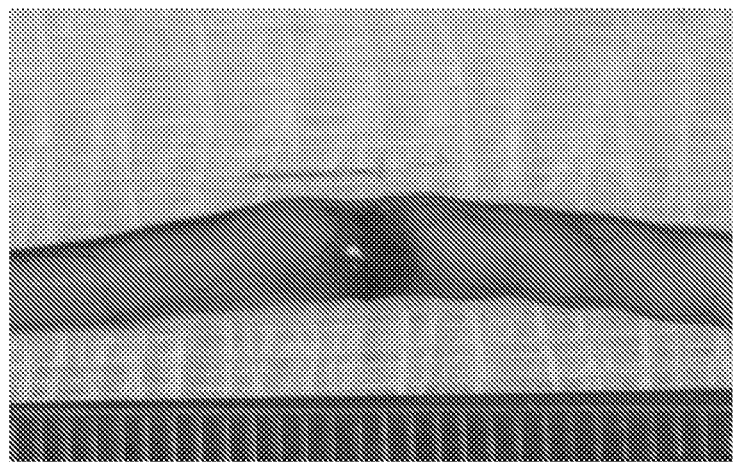
FIG. 11 is a photograph of a scarred canine vas of FIG. 10 after healing for 21 days.

FIG. 10 is a photograph of a thermally coagulated canine vas after being subject to the noninvasive laser vasectomy disclosed herein. FIG. 11 is a photograph of a scarred canine vas of FIG. 10 after healing for 21 days. The areas of the thermal lesion in FIG. 10 and scarred vas in FIG. 11 both measure approximately 3 mm long (parallel to the vas) and are full thickness through the diameter of the vas, about 2 to 3 mm.

In the specification and drawings, typical embodiments of the invention have been disclosed and, although specific terms have been employed, they have been used in a generic and descriptive sense only and not for purposes of limitation. Different kinds of materials and elements may be substituted for the parts disclosed herein, and the method steps can be adjusted yet still fall within the ambit of the invention. The invention is further set forth in the claims below.

REFERENCES

Incorporated Herein by Reference

1. A. Chandra, "Surgical sterilization in the United States: prevalence and statistics, 1965-1995," Vital Health Stat., vol. 23(20), pp. 1-41, 1998.
2. W. B. Miller, R. N. Shain, and D. J. Pasta, "Tubal sterilization or vasectomy: how do married couples make the choice," Feral. Steril., vol. 56, pp. 278-284, 1991.
3. N. W. Hendrix, S. P. Chauhan, and J. C. Morrison, "Sterilization and its consequences," Obstet. Gynecol. Surv., vol. 54, pp. 766-777, 1999.
4. R. N. Shain, W. B. Miller, and A. E. Holden, "Factors associated with married women's selection of tubal sterilization and vasectomy," Fertil. Steril., vol. 43, pp. 234-244, 1985.
5. M. Goldstein, "Surgical management of male infertility and other scrotal disorders," In Campbell's Urology, P. C. Walsh, A. B. Retik, E. D. Vaughan, and A. J. Wein A J, eds. Philadelphia: W. B. Saunders, vol. 2, pp. 1533-1587, 1998.
6. W. H. Weiske, "Vasectomy," Andrologia, vol. 33(3), pp. 124-134, 2001.
7. G. L. Smith, G. P. Taylor, and K. F. Smith, "Comparative risks and costs of male and female sterilization," Am. J. Public Health, vol. 75(4), pp. 370-374, 1985.
8. L. T. Strauss, C. M. Huezo, D. G. Kramer, R. W. Rochat, P. Senanayake, and G. L. Rubin, "Sterilization-associated deaths: a global survey," Int. J. Gynaecol. Obstet., vol. 22, pp. 67-75, 1984.
9. G. C. Denniston, "Vasectomy by electrocautery: outcomes in a series of 2,500 patients," J. Fam. Pract., vol. 21(1), pp. 35-40, 1985.
10. P. M. Alderman, "Complications in a series of 1224 vasectomies," J. Fam. Pract., vol. 33, pp. 579-584, 1991.
11. P. J. Schwingl and H. A. Guess, "Safety and effectiveness of vasectomy," Fertil. Steril., vol. 73(5), pp. 923-936, 2000.
12. S. Li, M. Goldstein, J. Zhu, and D. Huber, "The no-scalpel vasectomy," J. Urol., vol. 145, pp. 341-44, 1991.
13. S. L. Ban, "Sterility by vas injection method," Hu Nan Med. J., vol. 5, pp. 49-50, 1980.
14. S. Li, "Percutaneous injection of vas deferens," Chin. J. Urol., vol. 1(4), pp. 193-198, 1980.
15. T. Tao, "Vas deferens sterility by injection method," Qeng Dao Med. J., vol. 5, pp. 65-68, 1980.
16. J. O. Esho, G. W. Ireland, and A. Cass, "Comparison of ligation and fulguration methods," Urology, vol. 3(3), pp. 337-338, 1974.
17. S. S. Schmidt and T. M. Minckler, "The vas after vasectomy: comparison of cauterization methods," Urology, vol. 40(5), pp. 468-470, 1992.
18. T. R. L. Black, D. S. Gates, K. Lavely, and P. Lamptey, "The percutaneous electrocoagulation vasectomy technique—a comparative trial with the standard incision technique at marie stopes house, London," Contraception, vol. 39, pp. 359-368, 1989.
19. N. M. Fried, Y. D. Sinelnikov, B. Pant, W. W. Roberts, and S. B. Solomon, "Noninvasive vasectomy using a focused ultrasound clip: Thermal measurements and simulations," IEEE Trans. Biomed. Eng., vol. 48(12), pp. 1453-1459, 2001.
20. W. W. Roberts, D. Y. Chan, N. M. Fried, E. J. Wright, T. Nichol, T. W. Jarrett, L. R. Kavoussi, and S. B. Solomon, "High intensity focused ultrasound ablation of the vas deferens in a canine model," J. Urol., vol. 167, pp. 2613-2617, 2002.
21. A. Shafik, "Electrovasogram: a canine study of the electromechanical activity of the vas deferens," Urology, vol. 46(5), pp. 692-696, 1995.

The invention claimed is:

1. A system for use in noninvasive male sterilization procedures in which a vas deferens is thermally coagulated with a laser, the system comprising:
    an insulated vasectomy clamp for grasping the vas deferens and surrounding scrotal skin to secure a target area over a portion of the vasectomy clamp;
    a laser for irradiating a region within the target area, wherein the vas deferens in that region is thermally coagulated while remaining enclosed within the scrotal skin; and
    a cooling device for cooling at least a portion of the scrotal skin of the target area.

2. A system according to claim 1, wherein the cooling device directs a cooling spray onto the scrotal skin.

3. A system according to claim 1, wherein the cooling device directs a cryogen spray onto the scrotal skin.

4. A system according to claim 1, wherein the cooling device directs cold air onto the scrotal skin.

5. A system of claim 1, wherein said vasectomy clamp has at least two prongs and the prongs are thermally insulated.

6. A system of claim 1, wherein the vasectomy clamp comprises an insulating material that is transparent to near-infrared laser radiation and is also thermally insulating.

7. A system of claim 1, wherein the vasectomy clamp is insulated with an insulating material comprising fluorinated ethylene propylene copolymer.

8. A system of claim 1, wherein the vasectomy clamp has an inner diameter of approximately 3 mm to approximately 6 mm.

9. A system of claim 1 further comprising a means for holding the vasectomy clamp and positioning the target area under the laser.

10. A system according to claim 1, wherein said vasectomy clamp has at least two prongs, and the prongs are entirely surrounded by an insulating material that is thermally insulating and transparent to near-infrared laser radiation.

11. A method of noninvasive male sterilization comprising the steps of
grasping a vas deferens and surrounding scrotal skin with an insulated vasectomy clamp to secure a target area over a portion of the vasectomy clamp;
irradiating a region within the target area with a pulsed laser beam, wherein the vas deferens in that region is thermally coagulated without exposing the vas deferens;
cooling at least a portion of the scrotal skin of the target area with cryogen spray prior to and intermittently between laser pulses.

12. The method of claim 11, wherein said step of grasping a vas deferens comprises grasping the vas deferens with an insulated vasectomy clamp that is thermally insulated at the point at which the clamp contacts the skin.

13. The method of claim 12, wherein said step of grasping a vas deferens comprises grasping the vas deferens with prongs on the vasectomy clamp, said prongs being entirely surrounded by an insulating material that is thermally insulating and transparent to near-infrared laser radiation.

14. The method of claim 13, wherein said step of grasping a vas deferens comprises positioning the vas deferens over one of said prongs.

15. The method of claim 11, wherein scrotal skin is cooled with a cooling spray.

16. The method of claim 11, wherein scrotal skin is cooled with a cryogen spray.

17. A method of noninvasive male sterilization comprising the steps of positioning a vas deferens in a superficial position under the scrotal skin;
cooling at least a portion of the scrotal skin in a target area; and
irradiating a region within the target area with a laser, wherein the vas deferens in that region is thermally coagulated without exposing the vas deferens through the skin.

18. The method of claim 17, further comprising a step of grasping the vas deferens and surrounding scrotal skin with a vasectomy clamp to secure the target area over a portion of the vasectomy clamp prior to irradiating the region of the target area.

19. The method of claim 17, wherein the vasectomy clamp comprises an insulating material that is transparent to near-infrared laser radiation and is also thermally insulating.

20. The method of claim 19, wherein the insulating material comprises fluorinated ethylene propylene copolymer.

* * * * *